United States Patent [19]

Katsumi et al.

[11] 4,431,656
[45] Feb. 14, 1984

[54] 3,5-DI-TERT-BUTYLSTYRENE DERIVATIVES, SALTS THEREOF, AND PHARMACEUTICAL COMPOSITIONS CONTAINING THE SAME AS AN ACTIVE INGREDIENT

[75] Inventors: Ikuo Katsumi, Kobe; Hideo Kondo, Takasago; Katsuji Yamashita; Takayoshi Hidaka, both of Kobe; Kazunori Hosoe, Takasago; Yutaka Ariki, Himeji; Toshiaki Yamashita, Kakogawa; Kiyoshi Watanabe, Akashi, all of Japan

[73] Assignee: Kanegafuchi Chemical Industry Company Limited, Osaka, Japan

[21] Appl. No.: 337,168

[22] Filed: Jan. 5, 1982

[30] Foreign Application Priority Data

Feb. 5, 1981 [JP] Japan .................. 56-16602
Nov. 9, 1981 [JP] Japan .................. 56-179948

[51] Int. Cl.³ .................. A61K 31/415; C07D 307/26
[52] U.S. Cl. .................. 424/273 R; 424/279; 424/308; 424/331; 542/441; 542/442
[58] Field of Search .................. 542/449, 441, 442; 424/279, 331, 273 R

[56] References Cited

U.S. PATENT DOCUMENTS 4,128,664 12/1978 Moore .................. 424/324

FOREIGN PATENT DOCUMENTS 2518281 10/1975 Fed. Rep. of Germany ...... 542/449
44-17155 7/1969 Japan.

OTHER PUBLICATIONS

Van Der Goot et al, Eur. Med. Chem., No. 5, pp. 425-428, Sep.-Oct., 1978.

*Primary Examiner*—Jane T. Fan
*Attorney, Agent, or Firm*—Armstrong, Nikaido, Marmelstein & Kubovcik

[57] ABSTRACT

Novel compounds, 3,5-di-tert-butylstyrene derivatives and their salts, are disclosed, which derivatives are represented by the general formula:

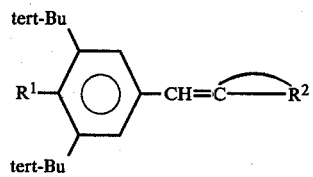

wherein $R^1$ stands for an acyloxy group represented by $R^3COO$ ($R^3$ is a hydrogen atom or an alkyl group with $C_1 \sim C_6$), an alkoxyl group of $R_4O$ ($R^4$ is an alkyl group with $C_1 \sim C_4$), a hydroxyl group, or a hydrogen atom; $R^2$ stands for

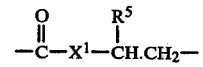

($R^5$ is a hydrogen atom or an alkyl group with $C_1 \sim C_3$ and $X^1$ is $CH_2$ or an oxygen atom),

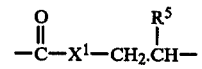

($R^5$ and $X^1$ are each the same as defined above), or

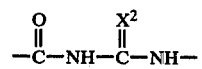

($X^2$ is an oxygen or sulfur atom).

There are also disclosed an anti-inflammatory, analgesic, and antipyretic pharmaceutical composition and an anti-platelet aggregation pharmaceutical composition, both pharmaceutical compositions comprising the foregoing 3,5-di-tert-butylstyrene derivative or its pharmaceutically acceptable salt as an active ingredient in association with pharmaceutical excipients.

28 Claims, No Drawings

3,5-DI-TERT-BUTYLSTYRENE DERIVATIVES, SALTS THEREOF, AND PHARMACEUTICAL COMPOSITIONS CONTAINING THE SAME AS AN ACTIVE INGREDIENT

BRIEF SUMMARY OF THE INVENTION

The present invention relates to a novel 3,5-di-tert-butylstyrene derivative, salts of its members capable of forming salts, and pharmaceutical compositions containing the same as an active ingredient.

The compound of the present invention (1) has anti-inflammatory, analgesic, and antipyretic activities in animal subjects. It has also an anti-platelet aggregation activity in animal subjects.

More specifically, the present invention relates to a novel 3,5-di-tert-butylstyrene derivative represented by the general formula (1):

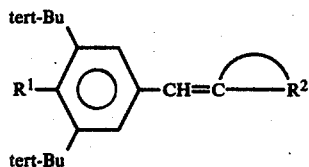

wherein $R^1$ stands for an acyloxy group represented by $R^3COO$ ($R^3$ is a hydrogen atom or an alkyl group with $C_1 \sim C_6$), an alkoxyl group of $R_4O$ ($R^4$ is an alkyl group with $C_1 \sim C_4$), a hydroxyl group, or a hydrogen atom; $R^2$ stands for

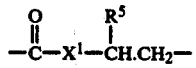

($R^5$ is a hydrogen atom or an alkyl group with $C_1 \sim C_3$ and $X^1$ is $CH_2$ or an oxygen atom),

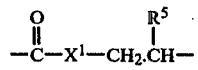

($R^5$ and $X^1$ are each the same as defined above), or

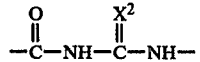

($X^2$ is an oxygen or sulfur atom), and salts of its members capable of forming salts. It further relates to pharmaceutical compositions, containing the same as an active ingredient, which are useful as an anti-inflammatory, analgesic and antipyretic agent, and an anti-platelet aggregation agent.

The present inventors have prepared a variety of 3,5-di-tert-butylstyrene derivatives and tested them extensively for pharmacological actions; as a result, the present inventors have completed the present invention based on the findings that novel compounds represented by the general formula (1) described above and their salts have excellent anti-inflammatory, analgesic, antipyretic, and anti-platelet aggregation activities.

DETAILED DESCRIPTION

1. Compounds

Of the compounds of the present invention (1), those in which $R^1$ is a hydroxyl group are capable of forming their salts with a base. The salts of the present invention may be any ones which can be formed from the compounds of the present invention and bases, specifically including, for example, (1) metal salts, especially those of alkali metals, alkaline earth metals, or aluminum, (2) ammonium salts, and (3) amine salts, especially those of methylamine, ethylamine, dimethylamine, diethylamine, triethylamine, pyrrolidine, piperidine, morpholine, hexamethyleneimine, aniline, pyridine, etc. For use as an anti-inflammatory, analgesic, and antipyretic agent, or an anti-platelet aggregation agent, physiologically acceptable salts should be chosen.

Representative examples of the compounds of the present invention are shown in Table 1.

TABLE 1

| Compound No. | R¹ | R² | Molecular formula | Crystal form | Melting point (°C.) | Elementary analysis | | | | | | | | |
|---|---|---|---|---|---|---|---|---|---|---|---|---|---|---|
| | | | | | | C | | H | | O | | N | | S |
| | | | | | | Found | Calcd | Found | Calcd | Found | Calcd | Found | Calcd | Found | Calcd |
| I | H— | —C(=O)—O—CH$_2$CH$_2$— | C$_{19}$H$_{26}$O$_2$ | leaflets | 112~114 | 79.75 | 79.68 | 9.11 | 9.15 | 11.14 | 11.17 | — | — | — | — |
| II | HO— | —C(=O)—O—CH$_2$CH$_2$— | C$_{19}$H$_{26}$O$_3$ | rods | 153~155 | 75.68 | 75.46 | 8.51 | 8.67 | 15.81 | 15.87 | — | — | — | — |
| III | CH$_3$COO— | —C(=O)—O—CH$_2$CH$_2$— | C$_{21}$H$_{28}$O$_4$ | plates | 144~146 | 73.16 | 73.22 | 8.23 | 8.19 | 18.61 | 18.58 | — | — | — | — |
| IV | CH$_3$CH$_2$COO— | —C(=O)—O—CH$_2$CH$_2$— | C$_{22}$H$_{30}$O$_4$ | plates | 107~108 | 73.59 | 73.71 | 8.40 | 8.44 | 18.01 | 17.85 | — | — | — | — |
| V | CH$_3$(CH$_2$)$_3$COO— | —C(=O)—O—CH$_2$CH$_2$— | C$_{24}$H$_{34}$O$_4$ | plates | 137~141 | 74.61 | 74.57 | 8.83 | 8.87 | 16.55 | 16.56 | — | — | — | — |
| VI | CH$_3$O— | —C(=O)—O—CH$_2$CH$_2$— | C$_{20}$H$_{28}$O$_3$ | rods | 130.5~132 | 75.88 | 75.91 | 8.92 | 8.92 | 15.20 | 15.17 | — | — | — | — |
| VII | CH$_3$CH$_2$O— | —C(=O)—O—CH$_2$CH$_2$— | C$_{21}$H$_{30}$O$_3$ | amorphous | — | 76.46 | 76.32 | 9.20 | 9.15 | 14.34 | 14.53 | — | — | — | — |
| VIII | HO— | —C(=O)—O—CHCH$_2$—<br>         CH$_3$ | C$_{20}$H$_{28}$O$_3$ | plates | 154~157 | 75.77 | 75.91 | 8.97 | 8.92 | 15.26 | 15.17 | — | — | — | — |
| IX | HO— | —C(=O)CH$_2$CH$_2$CH$_2$— | C$_{20}$H$_{28}$O$_2$ | plates | 146~148 | 80.05 | 79.96 | 9.53 | 9.39 | 10.42 | 10.65 | — | — | — | — |
| X | HO— | —C(=O)NH—C(=O)—NH— | C$_{18}$H$_{24}$N$_2$O$_3$ | needles | 243~245 | 68.24 | 68.33 | 7.58 | 7.65 | 15.09 | 15.17 | 9.09 | 8.85 | — | — |
| XI | HO— | —C(=O)NHCNH—<br>        ‖<br>        S | C$_{18}$H$_{24}$N$_2$O$_2$S | plates | 264~266 | 65.15 | 65.03 | 7.21 | 7.28 | 9.59 | 9.63 | 8.39 | 8.42 | 9.66 | 9.64 |

2. Preparation of compounds

There are, for example, the following ones as methods for synthesis of the compounds of the present invention represented by the general formula (1).

(1) According to a method reported by G. A. Howie et al. [Journal of Medicinal Chemistry 17, 840 (1974)], the desired compound can be synthesized by reacting a 3,5-di-tert-bytylbenzaldehyde compound represented by the general formula (2):

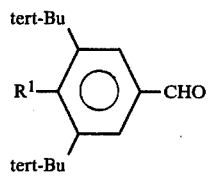

wherein $R^1$ stands for an acyloxy group of $R^3$COO ($R^3$ is a hydrogen atom or an alkyl group with $C_1$~$C_6$), an alkoxy group of $R^4$O ($R^4$ is an alkyl group with $C_1$~$C_4$), a hydroxyl group, or a hydrogen atom, either with an α-(triarylphosphoranylidene)-γ-butyrolactone compound represented by the general formula:

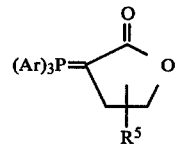

wherein Ar stands for an aryl group and $R^5$ stands for a hydrogen atom or an alkyl group with $C_1$~$C_3$, or with an α(triarylphosphoranylidene)-cyclopentanone compound represented by the general formula:

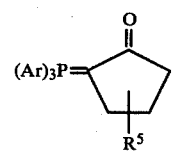

wherein Ar stands for an aryl group and $R^5$ stands for a hydrogen atom or an alkyl group with $C_1$~$C_3$. This method utilizes the so-called Wittig reaction; as ylide compounds to be reacted with the foregoing benzaldehyde derivative, ylide compounds derived from trialkylphosphine or triphenylarsine, in addition to the foregoing compounds, can also be used in the same manner.

(2) According to a method reported by H. Zimmer et al. [Journal of Organic Chemistry, 24, 28 (1959)], the desired compound can be synthesized by condensing a 3,5-di-tert-butylbenzaldehyde compound represented by the general formula (2):

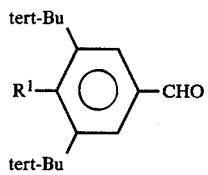

wherein $R^1$ stands for an acyloxy group of $R^3$COO ($R^3$ is a hydrogen atom or an alkyl group with $C_1$~$C_6$), an alkoxyl group of $R^4$O ($R^4$ is an alkyl group with $C_1$~$C_4$), a hydroxyl group, or a hydrogen atom, either with a compound represented by the general formula:

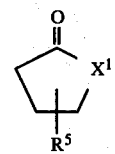

wherein $R^5$ stands for a hydrogen atom or an alkyl group with $C_1$~$C_3$ and $X^1$ stands for $CH_2$ or an oxygen atom, or with a compound represented by the general formula:

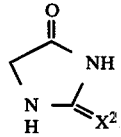

wherein $X^2$ stands for an oxygen or sulfur atom, in the presence of a base and an acid as a catalyst. The base which can be employed as a catalyst includes an alkali metal alcoholate such as sodium methylate and sodium ethylate; an alkali metal hydride such as sodium hydride and potassium hydride; an amine such as piperidine, morpholine, and ethanolamine; an alkali metal hydroxide such as potassium hydroxide and sodium hydroxide; an alkali metal amide such as lithium diisopropylamide; an alkali metal salt of an organic acid such as sodium acetate and potassium acetate; and so forth. The acid which can be employed as a catalyst includes boron trifluoride, titanium tetrachloride, p-toluenesulfonic acid, benzenesulfonic acid, and so forth.

(3) According to a method reported by S. Tsuboi et al. [Chemistry Letters, 1325 (1978)], the desired compound can be synthesized by reacting a 3,5-di-tert-butylbenzaldehyde compound represented by the general formula (2):

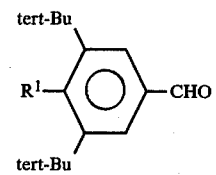

wherein $R^1$ represents an acyloxy group of $R^3$COO ($R^3$ is a hydrogen atom or an alkyl group with $C_1$~$C_6$), an alkoxyl group of $R^4$O ($R^4$ is an alkyl group with $C_1$~$C_4$), a hydroxyl group, or a hydrogen atom, with a compound represented by the general formula:

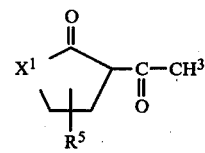

wherein $R^5$ stands for a hydrogen atom or an alkyl group with $C_1$~$C_3$ and $X^1$ stands for $CH_2$ or an oxygen atom, in the presence of a base such as potassium carbonate as a catalyst.

(4) The desired compound can be synthesized by a reaction between a 3,5-tert-butylbenzaldehyde compound represented by the general formula (2):

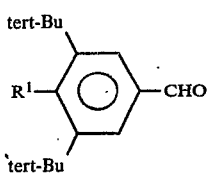

wherein $R^1$ stands for an acyloxy group of $R^3COO$ ($R^3$ is a hydrogen atom or an alkyl group with $C_1\sim C_6$), an alkoxyl group of $R^4O$ ($R^4$ is an alkyl group with $C_1\sim C^4$), a hydroxyl group, or a hydrogen atom, and the following compounds:

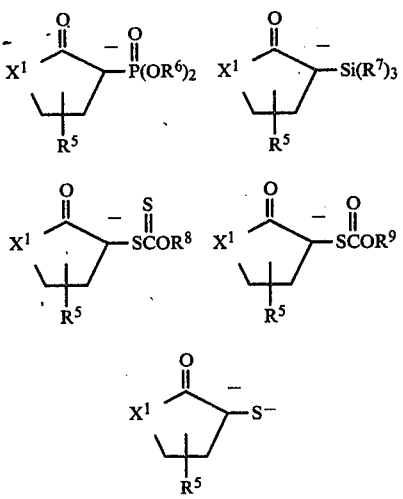

wherein $R^5$ stands for a hydrogen atom or an alkyl group with $C_1\sim C_3$, $R^{6},R^{7},R^{8}$ and $R^9$ each stands for an alkyl group, and $X^1$ stands for $CH_2$ or an oxygen atom.

(5) The desired compound can be synthesized by the Friedel-Crafts reaction, using a Lewis acid such as aluminum chloride and stannic chloride as a catalyst, between a 1,3-di-tert-butylbenzene compound represented by the general formula (3):

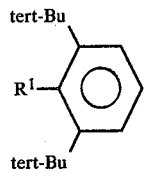

wherein $R^1$ stands for an acyloxy group of $R^3COO$ ($R^3$ is a hydrogen atom or an alkyl group with $C_1\sim C_6$), an alkoxyl group of $R^4O$ ($R^4$ is an alkyl group with $C_1\sim C^4$), a hydroxyl group, or a hydrogen atom, and compounds represented by the general formulas:

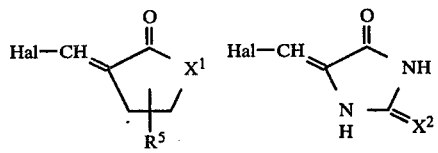

wherein $R^5$ stands for a hydrogen atom or an alkyl group with $C_1\sim C_3$, $X^1$ stands for $CH_2$ or an oxygen atom, $X^2$ stands for an oxygen or sulfur atom, and Hal stand for a halogen atom.

Of compounds represented by the general formula (1):

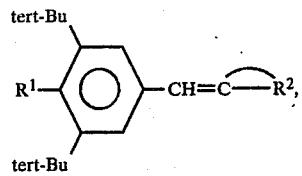

those in which $R^1$ stands for an acyloxy group of $R^3COO$ ($R^3$ is a hydrogen atom or an alkyl group with $C_1\sim C_6$ and $R^2$ $X^1$ each stands for the same as defined above can also be synthesized as follows: They can be synthesized either by (i) reacting a compound represented by the general formula (4), of compounds synthesized according to methods (1)~(5):

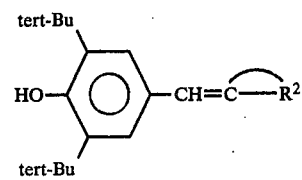

wherein $R^2$ stands for the same as defined above with an anhydride of an organic acid represented by $(R^{10}CO)_2O$ ($R^{10}$ is an alkyl group with $C_1\sim C_6$) in the presence of an acid such as sulfuric and p-toluenesulfonic acid or a base such as pyridine and lutidine, or by (ii) reacting a compound represented by the foregoing general formula (4) with an acid halide represented by $R^3COX^3$ ($R^3$ is a hydrogen atom or an alkyl group with $C_1\sim C_6$ and $X^3$ is a halogen atom) in the presence of an inorganic base, e.g. an alkali metal hydroxide such as sodium hydroxide or an organic base such as pyridine and triethylamine. In methods described above, the desired compound is synthesized by an esterification of a phenolic hydroxyl group; therefore, methods for obtaining the desired compound need not be limited to the foregoing methods and hence other reagents capable of effecting the esterification can also be used in the same manner.

Of the compounds represented by the general formula (1):

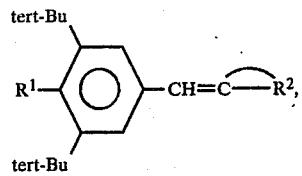

those in which $R^1$ stands for an alkoxyl group of $R^4O$ ($R^4$ is an alkyl group with $C_1\sim C_4$), and $R^2$ and $X^1$ are each the same as defined above can also be synthesized as follows.

They can be synthesized by reacting a compound, represented by the following general formula (4), which is synthesized by the foregoing methods (1)~(5):

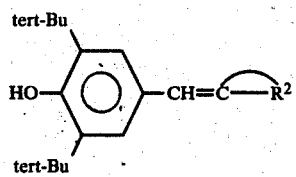

(4)

wherein $R^2$ stands for the same as defined above, with a diazoalkane represented by $R^{11}CHN_2$ ($R^{11}$ is a hydrogen atom or an alkyl group with $C_1\sim C_3$). Alternatively, they can be synthesized by reacting the compound (4) described above with alkyl halide represented by $R^4X^4$ (is an alkyl group with $C_1\sim C_4$ and $X^4$ is a halogen atom) in the presence of an inorganic base such as sodium hydride, potassium hydride, sodium amide, and potassium amide or an organic base such as 1,8-diazabicyclo[5.4.0] undec-7-ene. The foregoing methods are ones in which the desired compounds are synthesized by etherification of a phenolic hydroxyl group; therefore, methods for obtaining the desired compound need not be limited to the foregoing methods and hence other reagents capable of effecting the etherification can also be used in the same manner.

All alkyl groups appearing throughout the specification should be construed as comprising both straight-chain and branched-chain ones.

A method for preparation of α-(3,5-di-tert-butyl-4-hydroxybenzylidene)-γ-butyrolactone (Compounds II) will next be explained as a specific example of methods for preparation of the compounds of the present invention.

In dimethyl sulfoxide (DMSO) were dissolved 3,5-di-tert-butyl-4-hydroxybenzaldehyde and α-(triphenyl-phosphoranylidene)-γ-butyrolactone, and the reaction was carried out by heating the mixture at 80° C. in a hot water bath with stirring for 20 hours. After the completion of the reaction, chloroform was added to the cooled reaction mixture. DMSO was removed by washing the mixture with water and the chloroform layer separated. After the chloroform had been evaporated under reduced pressure, the residue was crystallized from ethanol, affording colorless rod-like crystals. The substance obtained here is colorless rod-like crystals which are insoluble in water, slightly soluble in methanol and ethanol, and readily soluble in tetrahydrofuran, chloroform, acetone, and DMSO, having the following properties:

Melting point 153°–155° C.
Molecular weight 302.42,

| Elementary analysis ($C_{19}H_{26}O_3$): | | |
|---|---|---|
| C | H | O |
| Found 75.68% | 8.51% | 15.81% |
| Calcd. 75.46% | 8.67% | 15.87% |

The structure of the compound (Compound II) was further confirmed by ultraviolet absorption spectrum, infrared absorption spectrum, and NMR spectrum.

3. Anti-inflammatory, analgesic and antipyretic agents, and anti-platelet aggregation agents The novel compounds of the foregoing general formula (1) and pharmaceutically acceptable salts thereof of the present invention are useful as anti-inflammatory, analgesic and antipyretic agents, and anti-platelet aggregation agents. These compounds possess excellent pharmacological activities and low toxicity, as shown in the following experiments. The compounds of the present invention are each indicated by the compound numbers shown in Table 1.

Anti-inflammatory activity (1) An acute anti-inflammatory activity was evaluated by the method of carrageenan-induced paw edema in rats [C. A. Winter et al., Proc. Soc. Exp. Biol. & Med., 111, 544 (1962)]. Six male Wistar strain rats weighing 150~180 g were used in each group. Test compounds suspended in 2.5% acacia were each administered p.o. to rats 1 hour before s.c. injection of 0.1 ml of 1% carrageenan in 0.9% NaCl into one hind paw. The volume of each paw edema was measured 3 and 5 hours after the injection of carrageenan. Percent edema inhibition was calculated by the following equation.

$$\text{Inhibition (\%)} = \left(1 - \frac{\text{Mean swelling volume of foot in the test group}}{\text{Mean swelling volume of foot in the control group}}\right) \times 100$$

The results are shown in Table 2.

TABLE 2

| Compound | Dose (mg/kg) | Inhibition (%) 3 hours | Inhibition (%) 5 hours |
|---|---|---|---|
| Compound I | 50 | 25.7 | 21.3 |
| Compound II | 50 | 29.7 | 36.7 |
| Compound III | 50 | 20.3 | 37.0 |
| Compound IV | 50 | 23.1 | 23.8 |
| Compound V | 50 | 22.8 | 18.8 |
| Compound VI | 50 | 35.5 | 24.3 |
| Compound VII | 50 | 25.0 | 29.5 |
| Compound VIII | 50 | 19.0 | 17.8 |
| Compound IX | 50 | 19.5 | 18.0 |
| Compound X | 50 | 33.9 | 18.5 |
| Compound XI | 50 | 32.4 | 27.0 |
| Indomethacin (known compound) | 5 | 28.4 | 32.5 |
| Phenylbutazone (Known compound) | 100 | 23.6 | 28.9 |

(2) A sub-chronic anti-inflammatory activity was evaluated by the method of paper disk-induced granuloma in rats [Y. Hara et al., Folia Pharmacol. Japon., 73, 557 (1977)].

Six male Wistar strain rats weighing 150–180 g were used in each group. Each paper disk (29±1 mg) was implanted s.c. into the bilateral area of scapula of rats under anesthesia with amobarbital sodium. Test compounds suspended in 2.5% acacia were each administered p.o. once daily for 7 days, starting on the day of surgery (day 0). The rats were killed on day 7, at which time the paper disks with surrounding granulomatous tissues were removed and dried to constant weight overnight, and weighed. Percent inhibition was calculated by the following equation.

$$\text{Inhibition (\%)} = \left(1 - \frac{\text{Mean dried granuloma weight in the test group}}{\text{Mean dried granuloma weight in the control group}}\right) \times 100$$

The results are shown in Table 3.

TABLE 3

| Compound | Dose (mg/kg/day) | Inhibition (%) |
|---|---|---|
| Compound II | 20 | 20.4 |
|  | 80 | 31.1 |
| Indomethacin (Known compound) | 5 | 28.8 |

(3) A chronic anti-inflammatory activity was evaluated by the method of adjuvant-induced arthritis in rats [D. T. Walz et al., J. Pharmacol. and Exp. Ther., 178, 223, (1971)]. Eight male Sprague-Dawley strain rats weighing 190~230 g were used in each group. Mycobacterium butyricum (0.5 mg) suspended in 0.05 ml of paraffin oil was injected i.d. into the left hind paw of rats. Test compounds suspended in 2.5% acacia were administered p.o. once daily for 21 days, starting on the day of the injection of an adjuvant (day 0). The volume of adjuvant-injected and uninjected feet was measured on day 14 and on day 21. Percent inhibition was calculated by the following equation.

$$\text{Inhibition (\%)} = \left(1 - \frac{\text{Mean swelling volume of foot in the test group}}{\text{Mean swelling volume of foot in the control group}}\right) \times 100$$

The results are shown in Table 4.

TABLE 4

| Compound | Dose (mg/kg/day) | Inhibition (%) Injected foot Day 14 | Injected foot Day 21 | Uninjected foot Day 14 | Uninjected foot Day 21 |
|---|---|---|---|---|---|
| Compound II | 20 | 29.5 | 50.4 | 65.7 | 71.2 |
|  | 80 | 42.9 | 54.2 | 91.4 | 71.2 |
| Indomethacin (Known compound) | 2 | 52.7 | 53.4 | 65.7 | 68.2 |
| Phenylbutazone (Known compound) | 100 | 45.5 | 53.4 | 91.4 | 63.6 |

Analgesic activity

An analgesic activity was evaluated by the method of acetic acid-induced writhing in mice [R. Koster et al., Federation Proc., 18, 412, (1959)]. Ten male ddY strain mice weighing 20~25 g were used in each group. Test compounds suspended in 2.5% acacia were each administered p.o. to the mice. One hour later, the mice were injected i.p. with 0.6% acetic acid in a volume of 0.1 ml/10 g body weight. The number of writhes in each of mice was counted for 20 minutes after the injection of the acetic acid. Percent inhibition was calculated by the following equation.

$$\text{Inhibition (\%)} = \left(1 - \frac{\text{Mean number of writhes in the test group}}{\text{Mean number of writhes in the control group}}\right) \times 100$$

The results are shown in Table 5.

TABLE 5

| Compound | Dose (mg/kg) | Inhibition (%) |
|---|---|---|
| Compound I | 100 | 31.8 |
| Compound II | 100 | 65.8 |
| Compound III | 100 | 53.1 |
| Compound IV | 100 | 33.0 |
| Compound V | 100 | 28.2 |
| Compound VI | 100 | 42.6 |
| Compound VII | 100 | 47.8 |
| Compound VIII | 100 | 47.2 |
| Compound IX | 100 | 47.2 |
| Compound X | 100 | 63.6 |
| Compound XI | 100 | 45.0 |
| Indomethacin (Known compound) | 5 | 44.1 |
| Aspirin (Known compound) | 100 | 38.0 |

Antipyretic activity

An antipyretic activity was evaluated by the Method of yeast-induced fever in rats [Y. Yanagi et al., *Folia Pharmacol. Japon.*, 74, 735 (1978)]. Five male Wistar strain rats weighing 150~180 g were used in each group. A 20% Baker's yeast suspension in 0.9% NaCl was injected s.c. into the dorsal region of rats in a volume of 1 ml/100 g body weight. Test compounds suspended in 2.5% acacia were each administered p.o. to rats with a rectal temperature of over 38.6° C., 18 hours after the injection of the yeast. The rectal temperature was determined with a thermometer, 1, 3 and 5 hours after the administration of test compounds. Percent inhibition was calculated by the following equation.

$$\text{Inhibition (\%)} = \left(1 - \frac{\text{Mean increase in rectal temperature in the test group}}{\text{Mean increase in rectal temperature in the control group}}\right) \times 100$$

The results are shown in Table 6.

TABLE 6

| Compound | Dose (mg/kg) | Inhibition (%) 1 hour | 3 hours | 5 hours |
|---|---|---|---|---|
| Compound I | 100 | 30.1 | 32.7 | 28.6 |
| Compound II | 100 | 32.3 | 53.3 | 64.9 |
| Compound III | 100 | 38.1 | 68.3 | 70.1 |
| Compound IV | 100 | 26.5 | 31.8 | 32.5 |
| Compound V | 100 | 29.2 | 31.4 | 33.8 |
| Compound VI | 100 | 39.2 | 59.1 | 72.7 |
| Compound VII | 100 | 33.6 | 40.0 | 48.1 |
| Compound VIII | 100 | 39.6 | 72.2 | 71.6 |
| Compound IX | 100 | 10.4 | 38.9 | 47.3 |
| Compound X | 100 | 13.5 | 17.8 | 21.4 |
| Compound XI | 100 | 32.7 | 50.0 | 52.6 |
| Indomethacin (Known compound) | 5 | 41.7 | 54.4 | 56.8 |

Inhibition of platelet aggregation

Inhibition of platelet aggregation was tested by the method of arachidonic acid-induced aggregation [J. B. Smith et al., J. Clinical Invest., 53, 1468 (1978)]. Platelet rich plasma (PRP) was prepared from rabbit blood containing 0.38% sodium citrate. To 0.9 ml of PRP was added at 37° C. 0.01 ml of varying concentrations of test compounds dissolved in methanol. One minute later, 0.05 ml of arachidonic acid (2 mg/ml) was added to the mixture to induce platelet aggregation. Inhibition of platelet aggregation was determined by a change in the light transmission. A concentration required for 100% transition of aggregation was expressed as an effective concentration

The results are shown in Table 7.

TABLE 7

| Compound | Effective concentration ($\mu$g/ml) |
| --- | --- |
| Compound I | 0.5 |
| Compound II | 0.1 |
| Compound III | 2.5 |
| Compound IV | 5.0 |
| Compound V | 5.0 |
| Compound VI | 0.5 |
| Compound VII | 1.0 |
| Compound VIII | 0.25 |
| Compound IX | 0.25 |
| Compound X | 5.0 |
| Compound XI | 2.5 |
| Aspirin (Known compound) | 150 |
| Indomethacin (Known compound) | 5.0 |

In addition to the foregoing in vitro test, inhibition of platelet aggregation by the compounds of the present invention was tested ex vivo in rats. Test compounds suspended in 2.5% acacia were each administered p.o. to rats in a dose of 100 mg/kg body weight. One hour later, blood samples were each taken from the rats and immediately mixed with an aqueous sodium citrate solution (final concentration of 0.33%). PRP was prepared from the blood mixture by centrifugation (1000 r.p.m., 10 minutes). Platelet aggregation was determined according to the method described above. Platelet aggregation of the blood from the compound-treated rats was compared with that of the blood from the control rats. The compounds of the present invention were found to be effective in inhibiting platelet aggregation induced by arachidonic acid.

Toxicity

Female ICR strain mice weighing 20~25 g in groups of six each were used for toxicity tests. Test compounds suspended in 2.5% acacia were administered p.o. to mice. The animals were observed daily for 14 days after the administration. The $LD_{50}$ values were estimated from mortality (No. of dead mice/No. of mice used).

The results are shown in Table 8.

TABLE 8

| Compound | $LD_{50}$ (mg/kg) |
| --- | --- |
| Compound I | >1000 |
| Compound II | >1000 |
| Compound III | >1000 |
| Compound IV | >1000 |
| Compound V | >1000 |
| Compound VI | >1000 |
| Compound VII | >1000 |
| Compound VIII | >1000 |
| Compound IX | >1000 |
| Compound X | >1000 |
| Compound XI | >1000 |

Moreover, the compounds of the present invention showed only small gastro-intestinal damages in rats.

Preparations and Dosage

The compounds of the present invention can be used as anti-inflammatory, analgesic and antipyretic agents in humans. They can also be used as anti-platelet aggregation agents in humans. For these purposes, the compounds can be administered orally, rectally, topically, or parenterally in a pharmaceutical dosage form, for example, tablets, capsules, granules, suppositories, ointments, syrups, injections and the like. These pharmaceutical dosage forms comprise the compounds and their pharmaceutically acceptable salts of the present invention as an active ingredient in association with pharmaceutical excipients, e.g., pharmaceutically acceptable organic or inorganic substances in either solid or liquid form, for example, crystalline cellulose, gelatin, lactose, starch, magnesium stearate, polyalkylene glycol, talc, fat, gum and the like. The content of the compounds of the present invention or their pharmaceutically acceptable salts in such compositions or preparations may be varied between 0.2 and 100% by weight. Furthermore, such compositions or preparations may contain other compatible pharamceutical agents including anti-inflammatory, analgesic, antipyretic or anti-platelet aggregation agents.

The pharmaceutical compositions or preparations are prepared so that a dosage unit contains between one and 5000 mg, preferably between three and 1000 mg of the active ingredient. The compounds and their salts of the present invention may be administered in a single dose, or preferably in divided doses. The dosage range of the pharmaceutical compositions or preparations containing the compounds and their salts of the present invention is from about 10 to about 10000 mg per man per day, preferably from about 20 to about 5000 mg per man per day based on the active ingredient.

The present invention will next be explained specifically by citing examples for preparation of the compounds of the present invention, but it is in no way limited to these examples.

Example 1 Synthesis of Compound I

In 10 ml of dimethyl sulfoxide (DMSO) were dissolved 0.43 g of 3.5-di-tert-butylbenzaldehyde and 0.63 g of $\alpha$-triphenylphosphosranylidene-$\gamma$-butyrolactone, and the reaction was carried out by heating the mixture at 80° C. with stirring for 2 hours. After the completion of the reaction, 100 ml of chloroform was added to the cooled reaction mixture. The mixture was washed 5 times with the same volume of water to remove the solvent DMSO. The chloroform layer was separated and concentrated to dryness under reduced pressure to remove the chloroform. Ethanol was added to the residue to effect crystallization. The crystals separated were further recrystallized from ethanol, giving 0.39 g (yield: 68%) of the desired Compound I.

Example 2 Synthesis of Compound II

In 150 ml of dimethyl sulfoxide (DMSO) were dissolved 18 g of 3.5-di-tert-butyl-4-hydroxybenzaldehyde and 27 g of $\alpha$-triphenylphosphoranylidene-$\gamma$-butyrolactone, and the reaction was carried out by heating the mixture at 80° C. in a hot water bath for 20 hours. After the completion of the reaction, 800 ml of chloroform was added to the cooled reaction mixture. The mixture was washed 5 times with the same volume of water to remove the solvent DMSO. The chloroform layer was separated and concentrated to dryness under reduced pressure to remove the chloroform. Ethanol was added to the residue to effect crystallization. The crystals separated were further recrystallized from ethanol, giving 18 g (yield: 77%) of the desired Compound II.

Example 3 Synthesis of Compound III

In 3.0 g of acetic anhydride was suspended 2.0 g of Compound II. A drop of concentrated sulfuric acid was added to and sufficiently mixed with the suspension, and the reaction was carried out by heating the mixture at 80° C. for 3 hours. After the completion of the reaction, the reaction mixture was poured onto crushed ice. The product, separating at first in an oily state, solidified gradually. The product, after total solidification, was collected by filtration and washed with water. The product obtained was crystallized by addition of ethanol and the crystals further recrystallized from ethanol, affording 1.8 g (yield: 79%) of Compound III.

Example 4 Synthesis of Compound IV

In 10 ml of propionic anhydride was suspended 3.0 g of Compound II. A drop of concentrated sulfuric acid was added to and sufficiently mixed with the suspension, and the reaction carried out by heating the mixture at 80° C. for 3 hours. The reaction mixture was worked up in the same manner as in Example 3, giving 1.47 g (yield: 41%) of the desired Compound IV.

Example 5 Synthesis of Compound V

In 10 ml of valeric anhydride was suspended 3.0 g of Compound II. A drop of concentrated sulfuric acid was added to and sufficiently mixed with the suspension, and the reaction carried out by heating the mixture at 80° C. for 3 hours. The reaction mixture was worked up in the same manner as in Example 3, giving 1.88 g (yield: 49%) of the desired Compound V.

Example 6 Synthesis of Compound VI

In 50 ml of tetrahydrofuran was dissolved 3 g of Compound II. To the solution was added 1 g of sodium hydride (oily, the content of 60%), and then 5 ml of methyl iodide, and the mixture was heated under reflux. The reaction mixture, allowed to cool, was poured into 100 ml of water. The resulting mixture, acidified with dilute sulfuric acid, was extracted twice with 100 ml of chloroform. The chloroform layer was washed twice with water, dried over anhydrous sodium sulfate, and the chloroform evaporated under reduced pressure. To a red syrup obtained was added n-hexane, whereupon the desired Compound V crystallized, giving 2.4 g (yield: 76%) of colorless crystals.

Example 7 Synthesis of Compound VII

In 50 ml of tetrahydrofuran was dissolved 3 g of Compound II. To the solution was added 1 g of sodium hydride (oily, the content of 60%), and then 6.4 ml of ethyliodide, and the mixture was heated under reflux for 3 hours. The reaction mixture was worked up in the same manner as in Example 6, giving 0.76 g (yield: 23%) of the desired Compound VII.

Example 8 Synthesis of Compound VIII

In 25 ml of DMSO were dissolved 3.3 g of 3.5-di-tert-butyl-4-hydroxybenzaldehyde and 5 g of α-triphenyl-phosphoranylidene-γ-valerolactone, and the reaction was carried out by heating the mixture at 80° C. in a hot water bath with stirring. After the completion of the reaction, 150 ml of chloroform was added to the cooled reaction mixture. The mixture was washed 5 times with the same volume of water to remove the solvent DMSO. The chloroform layer was separated and concentrated to dryness under reduced pressure to remove the chloroform. Crystallization was carried out by adding ethanol to the residue to obtain 1.5 g (yield: 34%) of the desired Compound VIII.

Example 9 Synthesis of Compound IX

In 60 ml of DMSO were dissolved 6 g of 3.5-di-tert-butyl-4-hydroxybenzaldehyde and 9 g of α-triphenyl-phosphoranylidene-cyclopentanone, and the reaction was carried out by heating the mixture at 80° C. in a hot water bath with stirring for 24 hours. After the completion of the reaction, 300 ml of chloroform was added to the cooled reaction mixture. The mixture was washed 5 times with the same volume of water to remove the solvent DMSO. The chloroform layer was separated and concentrated to dryness to remove the chloroform. The product was crystallized by adding ethanol to the residue. The crystals separated were further recrystallized twice from ethanol, giving 3.1 g (yield: 40%) of Compound IX.

Example 10 Synthesis of Compound X

To a mixed solvent of 40 ml of ethanol and 10 ml of water were added 11.7 g of 3.5-di-tert-butyl-4-hydroxybenzaldehyde and 5 g of hydantoin. To the mixture, warmed up to 70° C., was added 9.2 ml of ethanolamine. The mixture was further heated at 90° C. with stirring for 5 hours. After the completion of the reaction, 40 ml of water was added to the reaction mixture, whereupon precipitates formed, which were collected by filtration. For removal of the ethanolamine attached to the precipitates, the precipitates obtained above were again suspended in 100 ml of water, adjusted to pH 4.0 with 1 N hydrochloric acid, and again collected by filtration. The precipitates, washed sufficiently with water, were crystallized from acetone and then recrystallized twice from acetone, affording 1.5 g (yield: 9.5%) of Compound X.

Example 11 Synthesis of Compound XI

To 60 ml of ethanol were added 11.7 g of 3.5-di-tert-butyl-4-hydroxybenzaldehyde and 6.9 g of thiohydantoin. To the mixture, heated up to 80° C., was added 9.2 ml of ethanolamine. The mixture was further heated at 90° C. with stirring for 6 hours. After the completion of the reaction, 40 ml of water was added to the reaction mixture to form precipitates, which were collected by filtration. For removal of the ethanolamine attached to the precipitates, the precipitates obtained above were again suspended in 100 ml of water, adjusted to pH 4.0 with 1 N hydrochloric acid, and again collected by filtration. The precipitates obtained were dissolved in 100 ml of chloroform and sufficiently washed with 1 N hydrochloric acid, whereupon precipitates formed in chloroform. The precipitates were collected by filtration, crystallized from methanol, and further recrystallized from acetone, affording 0.9 g (yield: 5.4%) of Compound XI.

What is claimed is:

1. A 3,5-di-tert-butylstyrene derivative of the formula (1):

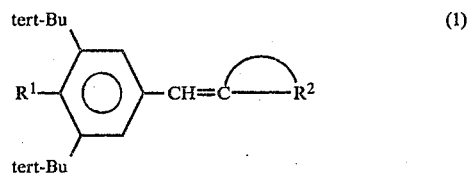

wherein
R¹ is R³COO, R⁴O or hydroxyl
R² is

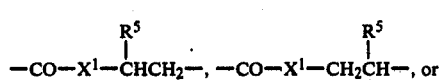

R³ is hydrogen or $C_1$-$C_6$ alkyl
R⁴ is $C_1$-$C_4$ alkyl
R⁵ is hydrogen or $C_1$-$C_3$ alkyl
X¹ is $CH_2$ or oxygen
X² is oxygen or sulfur
or a pharmaceutical salt thereof.

2. The 3,5-di-tert-butylstyrene derivative or a pharmaceutical salt thereof according to claim 1, wherein R² is:

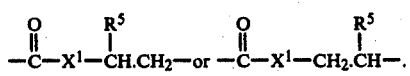

3. The 3,5-di-tert-butylstyrene derivative or a pharmaceutical salt thereof according to claim 1, wherein R² is:

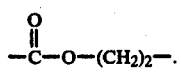

4. The 3,5-di-tert-butylstyrene derivative or a pharmaceutical salt thereof according to claim 1, wherein R² is:

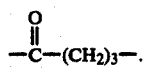

5. The 3,5-di-tert-butylstyrene derivative or a pharmaceutical salt thereof according to claim 1, wherein R² is:

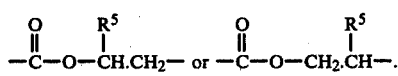

6. The 3,5-di-tert-butylstyrene derivative or a pharmaceutical salt thereof according to claim 1, wherein R¹ is a hydroxyl group and R² is:

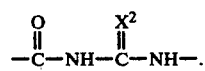

7. The 3,5-di-tert-butylstyrene derivative or a pharmaceutical salt thereof according to claim 1 represented by the formula:

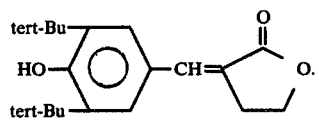

8. The 3,5-di-tert-butylstyrene derivative according to claim 1 represented by the formula:

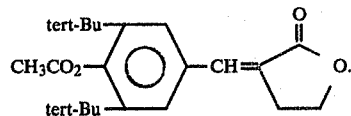

9. The 3,5-di-tert-butylstyrene derivative according to claim 1 represented by the formula:

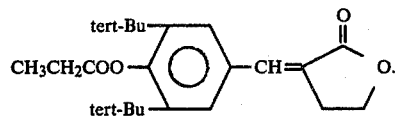

10. The 3,5-di-tert-butylstyrene derivative according to claim 1 represented by the formula:

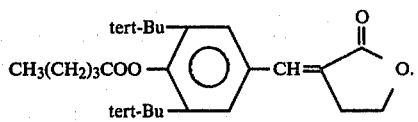

11. The 3,5-di-tert butylstyrene derivative according to claim 1 represented by the formula:

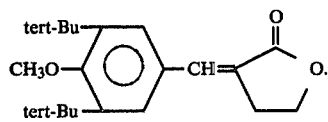

12. The 3,5-di-tert-butylstyrene derivative according to claim 1 represented by the formula:

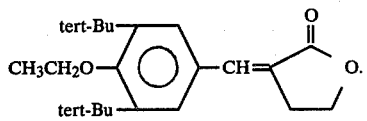

13. The 3,5-di-tert-butylstyrene derivative or a pharmaceutical salt thereof according to claim 1 represented by the formula:

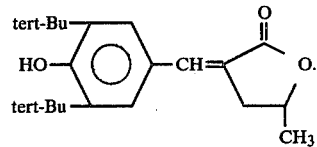

14. The 3,5-di-tert-butylstyrene derivative or a pharmaceutical salt thereof according to claim 1 represented by the formula:

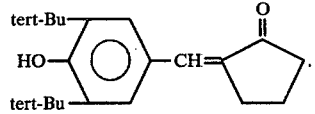

15. The 3,5-di-tert-butylstyrene derivative or a pharmaceutical salt thereof according to claim 1 represented by the formula:

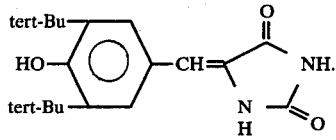

16. The 3,5-di-tert-butylstyrene derivative or a pharmaceutical salt thereof according to claim 1 represented by the formula:

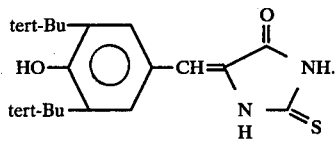

17. An anti-inflammatory, analgesic and antipyretic pharmaceutical composition which comprises an effective amount of the 3,5-di-tert-butylstyrene derivative of claim 1 or its pharmaceutically acceptable salt as an active ingredient in combination with pharmaceutical excipients.

18. An anti-inflammatory, analgesic, and antipyretic pharmaceutical composition which comprises an effective amount of the 3,5-di-tert-butylstyrene derivative of claim 2 or its pharmaceutically acceptable salt as an active ingredient in combination with pharmaceutical excipients.

19. An anti-inflammatory, analgesic, and antipyretic pharmaceutical composition which comprises an effective amount of the 3,5-di-tert-butylstyrene derivative of claim 3 or its pharmaceutically acceptable salt as an active ingredient in combination with pharmaceutical excipients.

20. An anti-inflammatory, analgesic, and antipyretic pharmaceutical composition which comprises an effective amount of the 3,5-di-tert-butylstyrene derivative of claim 4 or its pharmaceutically acceptable salt as an active ingredient in combination with pharmaceutical excipients.

21. An anti-inflammatory, analgesic, and antipyretic pharmaceutical composition which comprises an effective amount of the 3,5-di-tert-butylstyrene derivative of claim 5 or its pharmaceutically acceptable salt as an active ingredient in combination with pharmaceutical excipients.

22. An anti-inflammatory, analgesic, and antipyretic pharmaceutical composition which comprises an effective amount of the 3,5-di-tert-butylstyrene derivative of claim 6 or its pharmaceutically acceptable salt as an active ingredient in combination with pharmaceutical excipients.

23. An anti-platelet aggregation pharmaceutical composition which comprises an effective amount of the 3,5-di-tert-butylstyrene derivative of claim 1 or its pharmaceutically acceptable salt as an active ingredient in combination with pharmaceutical excipients.

24. An anti-platelet aggregation pharmaceutical composition which comprises an effective amount of the 3,5-di-tert-butylstyrene derivative of claim 2 or its pharmaceutically acceptable salt as an active ingredient in combination with pharmaceutical excipients.

25. An anti-platelet aggregation pharmaceutical composition which comprises an effective amount of the 3,5-di-tert-butylstyrene derivative of claim 3 or its pharmaceutically acceptable salt as an active ingredient in combination with pharmaceutical excipients.

26. An anti-platelet aggregation pharmaceutical composition which comprises an effective amount of the 3,5-di-tert-butylstyrene derivative of claim 4 or its pharmaceutically acceptable salt as an active ingredient in combination with pharmaceutical excipients.

27. An anti-platelt aggregation pharmaceutical composition which comprises an effective amount of the 3,5-di-tert-butylstyrene derivative of claim 5 or its pharmaceutically acceptable salt as an active ingredient in combination with pharmaceutical excipients.

28. An anti-platelet aggregation pharmaceutical composition which comprises an effective amount of the 3,5-di-tert-butylstyrene derivative of claim 6 or its pharmaceutically acceptable salts as an active ingredient in combination with pharmaceutical excipients.

* * * * *